United States Patent
Ralph et al.

(10) Patent No.: US 6,863,688 B2
(45) Date of Patent: Mar. 8, 2005

(54) INTERVERTEBRAL SPACER DEVICE UTILIZING A SPIRALLY SLOTTED BELLEVILLE WASHER HAVING RADIALLY SPACED CONCENTRIC GROOVES

(75) Inventors: James D. Ralph, Seaside Park, NJ (US); Stephen Tatar, Montvale, NJ (US)

(73) Assignee: SpineCore, Inc., Summit, NJ (US)

( * ) Notice: Subject to any disclaimer, the term of this patent is extended or adjusted under 35 U.S.C. 154(b) by 20 days.

(21) Appl. No.: 09/975,471

(22) Filed: Oct. 11, 2001

(65) Prior Publication Data

US 2002/0111685 A1 Aug. 15, 2002

Related U.S. Application Data

(63) Continuation-in-part of application No. 09/970,479, filed on Oct. 4, 2001.

(51) Int. Cl.$^7$ .................................................. A61F 2/44
(52) U.S. Cl. ................................ 623/17.13; 623/17.14; 623/17.15
(58) Field of Search ...................... 623/17.11, 17.13, 623/17.14, 17.15; 411/155, 156, 261, 544, 545

(56) References Cited

U.S. PATENT DOCUMENTS

| | | | |
|---|---|---|---|
| 2,193,122 A | * | 3/1940 | Crabbs ........................ 411/544 |
| 5,034,254 A | * | 7/1991 | Cologna et al. ......... 29/402.12 |
| 5,458,642 A | | 10/1995 | Beer et al. |
| 5,556,431 A | | 9/1996 | Buttner-Janz |
| 5,562,738 A | | 10/1996 | Boyd et al. |
| 5,674,296 A | | 10/1997 | Bryan et al. |
| 5,676,701 A | | 10/1997 | Yuan et al. |
| 5,676,702 A | | 10/1997 | Ratron |
| 5,683,465 A | | 11/1997 | Shinn et al. |
| 5,755,796 A | | 5/1998 | Ibo et al. |
| 5,827,328 A | | 10/1998 | Buttermann |
| 5,865,846 A | | 2/1999 | Bryan et al. |
| 5,888,226 A | | 3/1999 | Rogozinski |
| 5,895,428 A | | 4/1999 | Berry |
| 5,899,941 A | | 5/1999 | Nishijima |
| 5,989,291 A | | 11/1999 | Ralph et al. |
| 6,001,130 A | | 12/1999 | Bryan et al. |
| 6,019,792 A | | 2/2000 | Cauthen |
| 6,039,763 A | | 3/2000 | Shelokov |
| 6,063,121 A | | 5/2000 | Xavier et al. |
| 6,113,637 A | | 9/2000 | Gill et al. |
| 6,136,031 A | | 10/2000 | Middleton |
| 6,146,421 A | | 11/2000 | Gordon et al. |
| 6,156,067 A | | 12/2000 | Bryan et al. |
| 6,179,874 B1 | | 1/2001 | Cauthen |
| 6,228,118 B1 | | 5/2001 | Gordon |

* cited by examiner

*Primary Examiner*—Brian E Pellegrino
(74) *Attorney, Agent, or Firm*—Lerner, David, Littenberg, Krumholz & Mentlik, LLP

(57) ABSTRACT

An intervertebral spacer device having a pair of opposing plates for seating against opposing vertebral bone surfaces, separated by at least one spring mechanism. The preferred spring mechanism is at least one spirally slotted belleville washer having radially spaced concentric grooves. In a preferred embodiment there is a single such belleville washer which is modified to mount onto a ball-shaped head. The lower plate of this embodiment includes a post extending upwardly from the inner surface of the plate, the post including a ball-shaped head. The modified belleville washer can be rotatably mounted to the head such that the wider portion of the washer seats against the upper plate.

12 Claims, 5 Drawing Sheets

INTERVERTEBRAL SPACER DEVICE UTILIZING A SPIRALLY SLOTTED BELLEVILLE WASHER HAVING RADIALLY SPACED CONCENTRIC GROOVES

CROSS-REFERENCE TO RELATED APPLICATION

This application is a continuation-in-part of U.S. patent application Ser. No. 09/790,479, filed Oct. 4, 2001, which is fully incorporated herein by reference.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device which utilizes a spirally slotted belleville washer, having radially spaced concentric grooves, as a restoring force generating element.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of a spring mechanism. In particular, this spring mechanism provides a strong restoring force when a compressive load is applied to the plates, and may also permit rotation of the two plates relative to one another. While there are a wide variety of embodiments contemplated, a preferred embodiment includes a belleville washer utilized as the restoring force providing element, the belleville washer being spirally slotted and having radially spaced concentric grooves.

More particularly, as the assembly is to be positioned between the facing surfaces of adjacent vertebral bodies, the base plates should have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates can include a porous coating into which the bone of the vertebral body can grow. (Note that this limited fusion of the bone to the base plate does not extend across the intervertebral space.)

In some embodiments (not in the preferred embodiment), between the base plates, on the exterior of the device, there is included a circumferential wall which is resilient and which simply prevents vessels and tissues from entering within the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials that could be utilized herein may be found in the field of orthopedic in conjunction with ligament and tendon repair. It is anticipated that future developments in this area will produce materials that are compatible for use with this invention, the breadth of which shall not be limited by the choice of such a material.

As introduced above, the internal structure of the present invention comprises a spring member, which provides a restoring force when compressed. More particularly, it is desirable that the restoring forces be directed outward against the opposing plates, when a compressive load is applied to the plates. In addition, in certain embodiments, it is necessary that the restoring force providing subassembly not substantially interfere with the rotation of the opposing plates relative to one another. In the preferred embodiment, the spring subassembly is configured to allow rotation of the plates relative to one another. In other embodiments, the spring subassembly can be configured to either allow rotation of the plates, or prevent rotation of the plates (through the tightening of a set screw as discussed below). As further mentioned above, the force restoring member comprises at least one belleville washer.

Belleville washers are washers which are generally bowed in the radial direction. Specifically, they have a radial convexity (i.e., the height of the washer is not linearly related to the radial distance, but may, for example, be parabolic in shape). The restoring force of a belleville washer is proportional to the elastic properties of the material. In addition, the magnitude of the compressive load support and the restoring force provided by the belleville washer may be modified by providing slots and/or grooves in the washer. In the preferred embodiment of the present invention, the belleville washer utilized as the force restoring member is spirally slotted, with the slots initiating on the periphery of the washer and extending along arcs which are generally radially inwardly directed a distance toward the center of the bowed disc, and has radially uniformly spaced concentric grooves of uniform width and depth.

As a compressive load is applied to a belleville washer, the forces are directed into a hoop stress which tends to radially expand the washer. This hoop stress is counterbalanced by the material strength of the washer, and the strain of the material causes a deflection in the height of the washer. Stated equivalently, a belleville washer responds to a compressive load by deflecting compressively, but provides a restoring force which is proportional to the elastic modulus of the material in a hoop stressed condition. With slots and/or radially spaced concentric grooves formed in the washer, it expands and restores itself far more elastically than a solid washer.

In general, the belleville washer is one of the strongest configurations for a spring, and is highly suitable for use as a restoring force providing subassembly for use in an intervertebral spacer element which must endure considerable cyclical loading in an active human adult.

In the preferred embodiment of the present invention, a single modified belleville washer, which is of the slotted variety and has radially spaced concentric grooves as described above, is utilized in conjunction with a ball-shaped post on which it is free to rotate through a range of angles (thus permitting the plates to rotate relative to one another through a corresponding range of angles). More particularly, this embodiment comprises a pair of spaced apart base plates, one of which is simply a disc shaped member (preferably shaped to match the end of an intervertebral disc) having an external face (having the porous coating discussed above) and an internal face having an annular retaining wall (the purpose of which will be discussed below). The other of the plates is similarly shaped, having an exterior face with a porous coating, but further includes on its internal face a central post portion which rises out of the internal face at a nearly perpendicular angle. The top of this post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, a modified and spirally slotted belleville washer having radially spaced concentric grooves is mounted to this ball-shaped knob in such a way that it may rotate freely through a range of angles equivalent to the fraction of normal human spine rotation (to mimic normal disc rotation). The belleville washer of this design is modified by including an enlarged inner circumferential portion (at the center of the washer) which accommodates the ball-shaped portion of the post. More particularly, the enlarged portion of the modified belleville washer includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the belleville washer. Subsequent introduction of the set screw into the axial bore of the post prevents the ball-shaped head from deflecting. Thereby, the washer can be secured to the ball-shaped head so that it can rotate thereon through a range of proper lordotic angles (in some embodiments, a tightening of the set screw locks the washer on the ball-shaped head at one of the lordotic angles).

This assembly provides ample spring-like performance with respect to axial compressive loads, as well as long cycle life to mimic the axial biomechanical performance of the normal human intervertebral disc. The spiral slots and radially spaced concentric grooves of the belleville washer allow the washer to expand radially as the slots and grooves widen under the load, only to spring back into its undeflected shape upon the unloading of the spring. As the washer compresses and decompresses, the annual retaining wall maintains the wide end of the washer within a prescribed boundary on the internal face of the base plate which it contacts, and an annular retaining ring maintains the wide end of the washer against the internal face.

Finally, inasmuch as the human body has a tendency to produce fibrous tissues in perceived voids, such as may be found within the interior of the present invention, and such fibrous tissues may interfere with the stable and/or predicted functioning of the device, some embodiments of the present invention (although not the preferred embodiment) will be filled with a highly resilient elastomeric material. The material itself should be highly biologically inert, and should not substantially interfere with the restoring forces provided by the springlike mechanisms therein. Suitable materials may include hydrophilic monomers such as are used in contact lenses. Alternative materials include silicone jellies and collagens such as have been used in cosmetic applications. As with the exterior circumferential wall, which was described above as having a variety of suitable alternative materials, it is anticipated that future research will produce alternatives to the materials described herein, and that the future existence of such materials which may be used in conjunction with the present invention shall not limit the breadth thereof.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
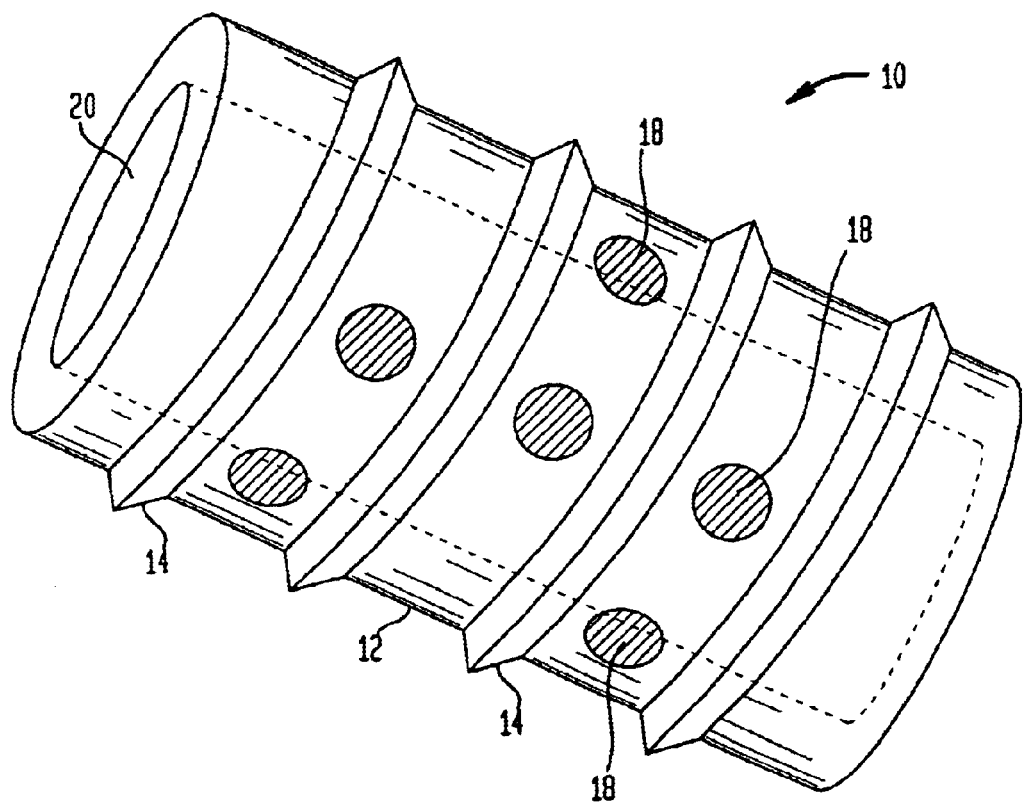
FIG. 1 is a side perspective view of an interbody fusion device of the prior art.
Figure 2:
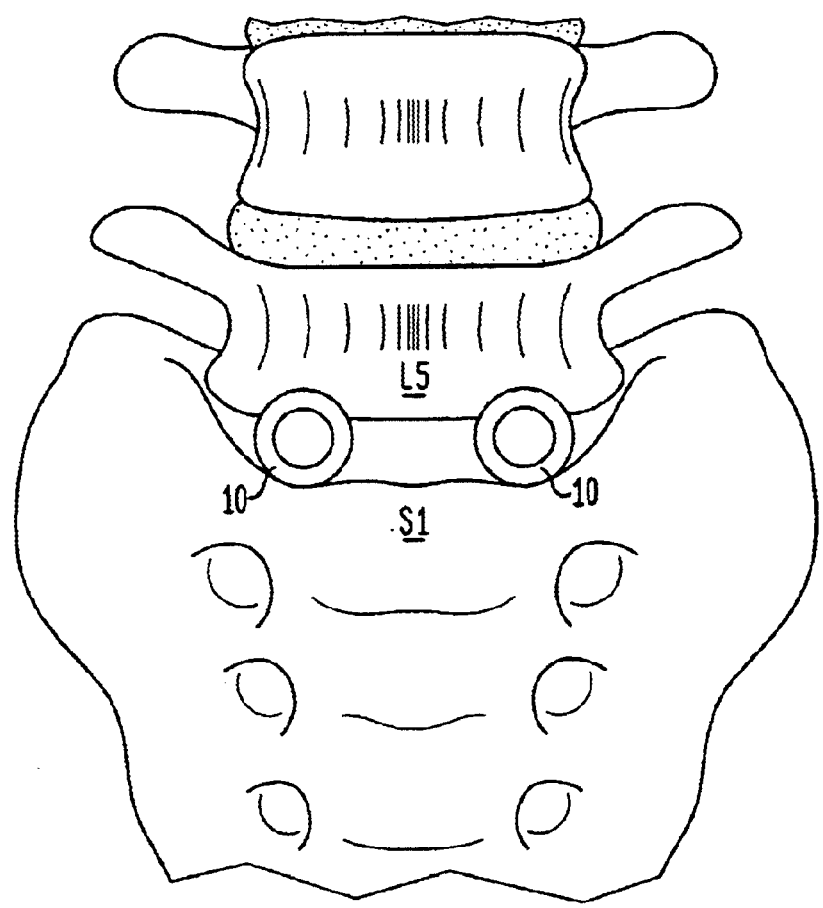
FIG. 2 is a front view of the anterior portion of the lumbo-sacral region of a human spine, into which a pair of interbody fusion devices of the type shown in FIG. 1 have been implanted.
Figure 3A:
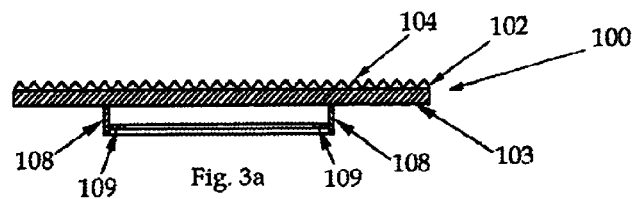
FIGS. 3a and 3b are side cross-section views of the upper and lower opposing plates of the preferred embodiment of the present invention.
Figure 3B:
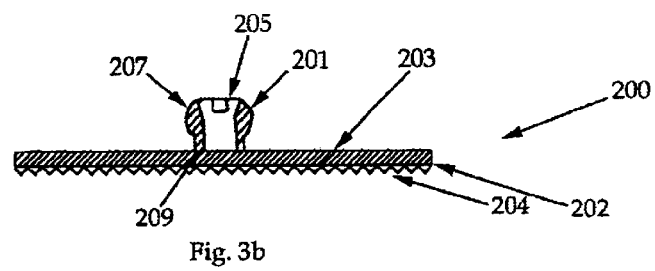

Referring now to FIGS. 3a and 3b, side cross-section views of upper and lower plate members 100, 200 of the preferred embodiment of the present invention are shown. As the device is designed to be positioned between the facing surfaces of adjacent vertebral bodies, the plates include substantially flat external face portions 102, 202 which seat against the opposing bone surfaces. In addition, the plates are to mate with the bone surfaces in such a Ail way as to not rotate relative thereto. It is, therefore, preferred that the external faces of the plates include a porous coating 104, 204 into which the bone of the vertebral body can grow. (Note that this limited fusion of the bone to the base plate does not extend across the intervertebral space.) A hole (not shown) can be provided in the upper plate such that the interior of the device may be readily accessed if a need should arise.

The upper plate 100 includes an internal face 103 that includes an annular retaining wall 108 and an annular retaining ring 109. The lower plate 200 includes an internal face 203 that includes a central post member 201 which rises out of the internal face 203 at a nearly perpendicular angle. The top of this post member 201 includes a ball-shaped head 207. The head 207 includes a series of slots which render it compressible and expandable in correspondence with a radial pressure (or a radial component of a pressure applied thereto). The head 207 includes a central threaded axial bore 209 which extends down the post 201. This threaded bore 209 is designed to receive a set screw 205. Prior to the insertion of the set screw 205, the ball-shaped head 207 of the post 201 can deflect radially inward because of the slots (so that the ball-shaped head contracts). The insertion of the set screw 205 eliminates the capacity for this deflection.

Figure 4A:
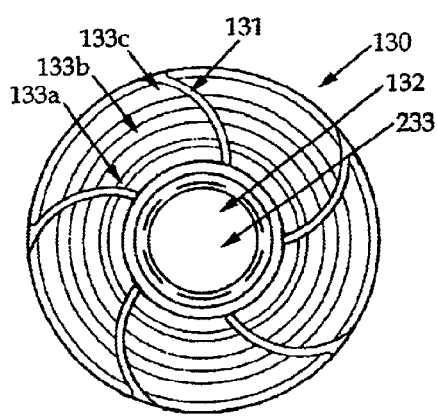
FIGS. 4a and 4b are top and side cross-section view of a belleville washer having radially uniformly spaced concentric grooves of uniform width and depth and spiral slots, for use in a preferred embodiment of the present invention.
Figure 4B:
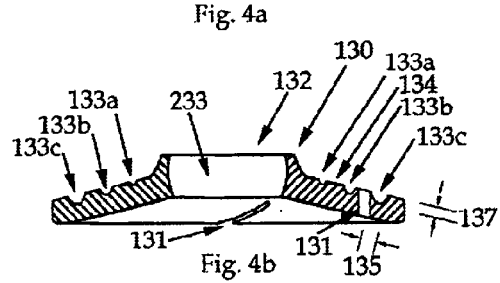

Referring now to FIGS. 4a and 4b, a spirally slotted belleville washer 130 having radially spaced concentric grooves is provided in top and side cross-section views. The belleville washer 130 is a restoring force providing device which comprises a circular shape, having a central opening 132, and which is radially arched in shape. The belleville washer 130 has a radial convexity 134 (i.e., the height of the washer 130 is not linearly related to the radial distance, but may, for example, be parabolic in shape). The restoring force of the belleville washer 130 is proportional to the elastic properties of the material.

The belleville washer 130 comprises a series of spiral slots 131 formed therein. The slots 131 extend from the outer edge of the belleville washer, inward along arcs generally directed toward the center of the element. The slots 131 do not extend fully to the center of the element. In preferred embodiments, the slots may extend anywhere from a quarter to three quarters of the overall radius of the washer, depending upon the requirements of the patient, and the anatomical requirements of the device.

The belleville washer 130 further comprises a series of grooves 133 formed therein. The grooves 133 are concentric and radially spaced from the outer edge of the belleville washer toward the center of the element. In the preferred embodiment shown in FIGS. 4a and 4b, the width 135 of each groove 133 is uniform along the length of the groove 133. Further in the preferred embodiment, the depth 137 of each groove 133 is uniform along the length of the groove 133. Further in the preferred embodiment, each groove 133 has a different width configuration and a different depth configuration than each other groove 133. More specifically, in the preferred embodiment, the width dimension and the depth dimension both vary from groove to groove, each increasing incrementally from groove to adjacent groove with increasing distance from the center of the washer 130. Stated alternatively, grooves that are relatively more narrow and more shallow than the other grooves are closer to the center of the washer, whereas grooves that are relatively wider and deeper than the other grooves are closer to the outer edge of the washer. This is illustrated by example in FIGS. 4a and 4b, which show three concentric grooves 133a–c, with the outermost groove 133c being deeper and wider than groove 133b, which is in turn deeper and wider than groove 133a. Further in the preferred embodiment, the radial spacing of the grooves is uniform.

Figure 5A:
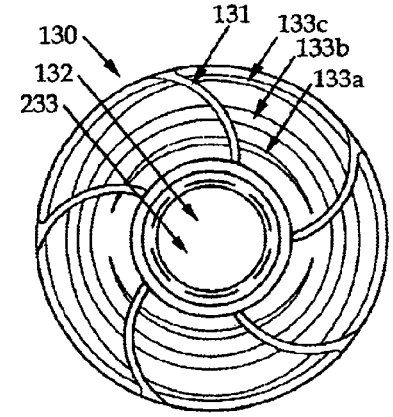
FIGS. 5a–5c are top and side cross-section views of a belleville washer having radially non-uniformly spaced concentric grooves of varying width and depth and spiral slots, for use in an alternate embodiment of the present invention.
Figure 5C:
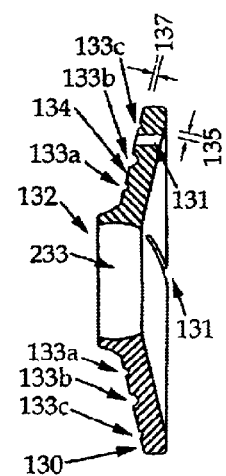
Figure 5B:
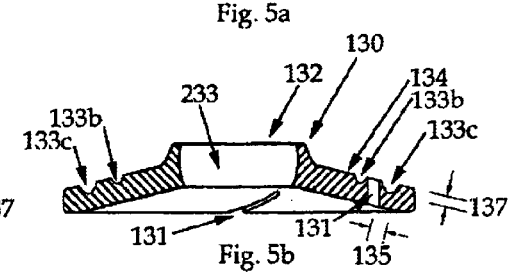

It should be understood that in other embodiments, one or both of the depth and the width of each groove can be (1) increasing along the length of the groove, (2) decreasing along the length of the groove, or (3) varied along the length of each groove, either randomly or according to a pattern. Moreover, in other embodiments, it can be the case that each groove is not formed similarly to one or more other grooves, with or without respect to width and depth dimensions, but rather one or more grooves are formed in any of the above-mentioned fashions, while one or more other grooves are formed in another of the above-mentioned fashions or other fashions. Also, in other embodiments, it can be the case that the radial distance between the grooves is not the same, but rather the spacing increases the closer the space is to the outer edge of the washer, decreases the closer the space is to the outer edge of the washer, or varies either randomly or according to a pattern. Also, while the grooves of the preferred embodiment and the illustrated alternate embodiment have lengths that form closed loops, it should be noted that in other embodiments, the concentric grooves can have lengths that form open loops or arcs; for example, a two concentric grooves forming open loops or arcs can be used in place of a single concentric groove forming a closed loop. It should be clear that any concentric groove pattern can be implemented without departing from the scope of the present invention. To illustrate an alternate embodiment showing an alternate radially spaced concentric groove pattern, FIGS. 5a–5c show a belleville washer 130 having radially spaced concentric grooves 133 in top and side cross-section views, with each groove 133 having a width and a depth each varying along the length of the groove 133, with each groove 133 being formed differently than at least one other groove 133, with the radial spacing of the grooves 133 being varied, and with both closed loops and open loops or arcs being used. In this alternate embodiment, the difference between the grooves 133 is characterized in that the wider and deeper portion of any particular groove 133 is on a different side of the washer 130 than the wider and deeper portion of at least one other groove 133.

As a compressive load is applied to the belleville washer 130 of the present invention, the forces are directed into a hoop stress which tends to radially expand the washer. This hoop stress is counterbalanced by the material strength of the washer, and the force necessary to widen the spiral slots 131 and the radially spaced concentric grooves 133 along with the strain of the material causes a deflection in the height of the washer. Stated equivalently, the belleville washer 130 responds to a compressive load by deflecting compressively; the spiral slots and/or radially spaced concentric grooves cause the washer to further respond to the load by spreading as the slots and/or the grooves in the washer expand under the load. The spring, therefore, provides a restoring force which is proportional to the elastic modulus of the material in a hoop stressed condition.

More particularly, the central opening 132 of the belleville washer is enlarged. This central opening 132 includes a curvate volume 233 for receiving therein the ball-shaped head 207 of the post 201 of the lower plate 200 described above. More particularly, the curvate volume 233 has a substantially constant radius of curvature which is also substantially equivalent to the radius of the ball-shaped head 207 of the post 201. In this embodiment, the spiral slots 131 do not extend all the way to the central opening 132, and approach the opening only as far as the material strength of the washer can handle without plastically deforming under the expected anatomical loading. Preferably, the center of the washer is flat; therefore, the central opening 132 can be formed from flat edges. It should be understood that this is not required, but rather is preferred.

Figure 6A:
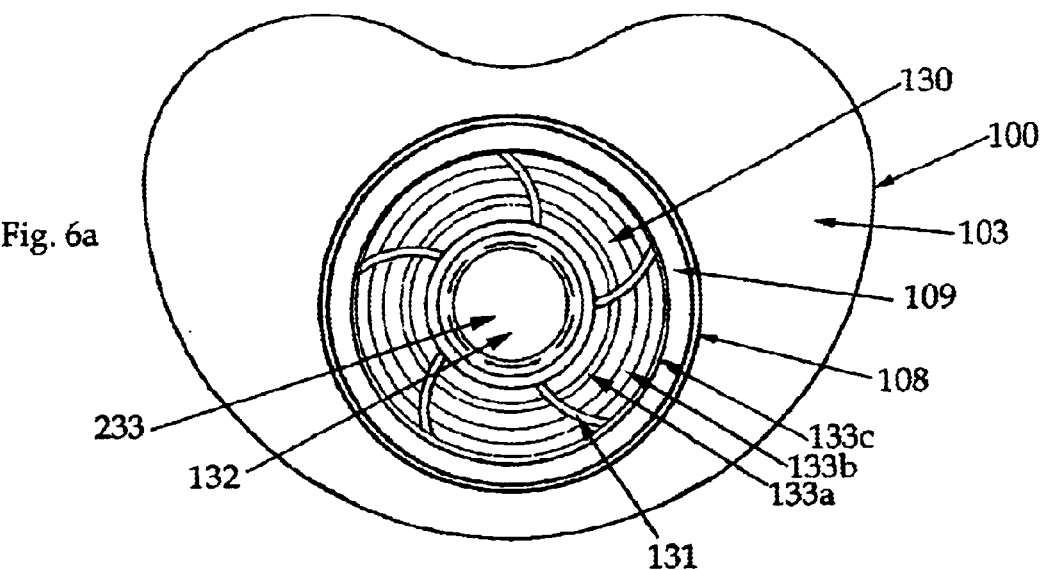
FIG. 6a is a top view of the upper plate of FIG. 3a, with the belleville washer of FIGS. 4a and 4b fitted within a retaining wall and a retaining ring of the upper plate.
Figure 6B:
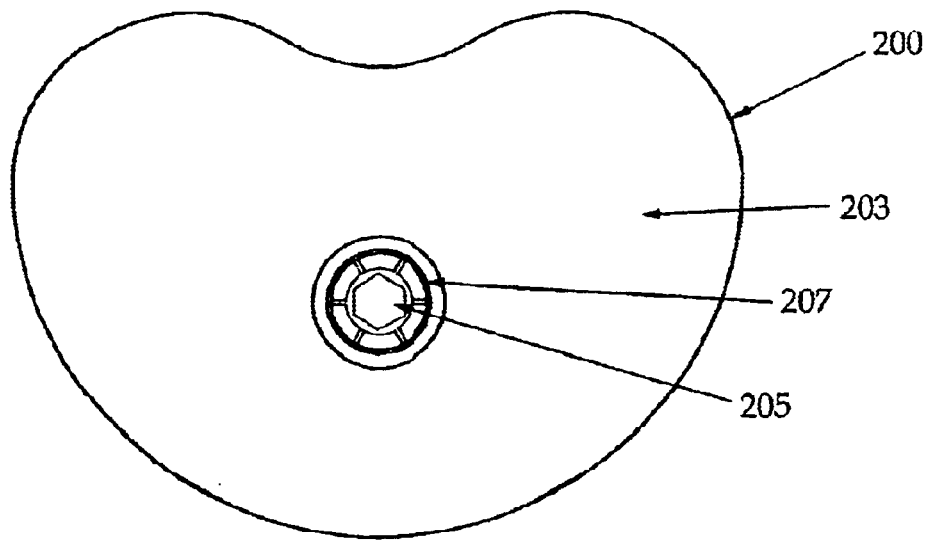
FIG. 6b is a top view of the lower plate of FIG. 3b.

Referring now to FIG. 6a, a top view of the upper plate 100 of FIG. 3a, with the spirally slotted and concentrically grooved belleville washer 130 of FIGS. 4a and 4b fitted within a retaining wall 108 and a retaining ring 109 of the upper plate 100, is shown. The diameter of the retaining wall 108 is preferably slightly wider than the diameter of the undeflected belleville washer 130 such that the loading thereof can result in an unrestrained radial deflection of the washer 130. FIG. 6b shows a top view of the lower plate 200 of FIG. 3b.

Figure 7:
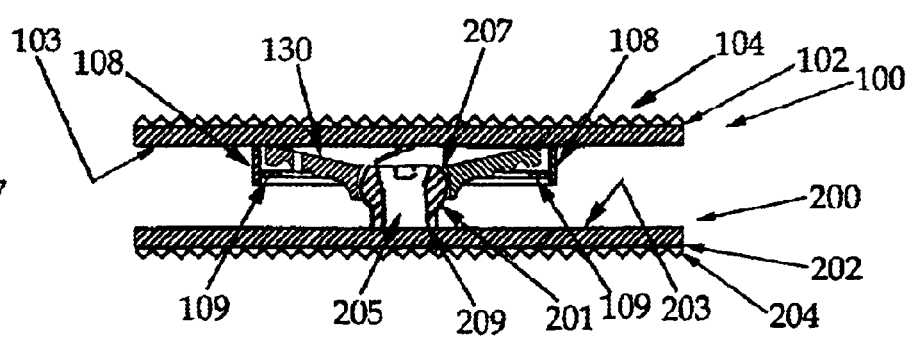
FIG. 7 is a side cross-section view of the preferred embodiment of the present invention, which utilizes a belleville washer of the type shown in FIGS. 4a and 4b, showing the plates of FIGS. 6a and 6b assembled together.

FIG. 7 shows the fully assembled preferred embodiment of the present invention. The spirally slotted and radially grooved belleville washer 130 of FIGS. 4a and 4b is placed with its wide end against the top plate 100 within the annular retaining wall 108 as shown in FIG. 6b. The annular retaining ring 109 is provided to hold the belleville washer 130 against the internal face 103 of the upper plate 100 within the retaining wall 108. The post 201 of the lower plate 200 is fitted into the central opening 132 of the belleville washer 130 (the deflectability of the ball-shaped head 207 of the post 201, prior to the insertion of the set screw 205, permits the head 207 to be inserted into the interior volume 233 at the center of the belleville washer 130. Subsequent introduction of the set screw 205 into the axial bore 209 of the post 201 eliminates the deflectability of the head 207 so that the washer 130 cannot be readily removed therefrom, but can still rotate thereon. In some embodiments (not in this preferred embodiment), the post head 207 can be locked tightly within the central volume 233 of the belleville washer 130 by the tightening of the set screw 205, to prevent any rotation of the plates 100, 200. Compressive loading of the assembly causes the washer 130 to deflect (with the spiral slots and the radially spaced concentric grooves enhancing the deflection) so that the wide end radially expands while being maintained centrally against the upper plate 100 by the retaining wall 108 and the retaining ring 109. When the load is removed, the washer 130 springs back to its original shape.

Figure 8A:
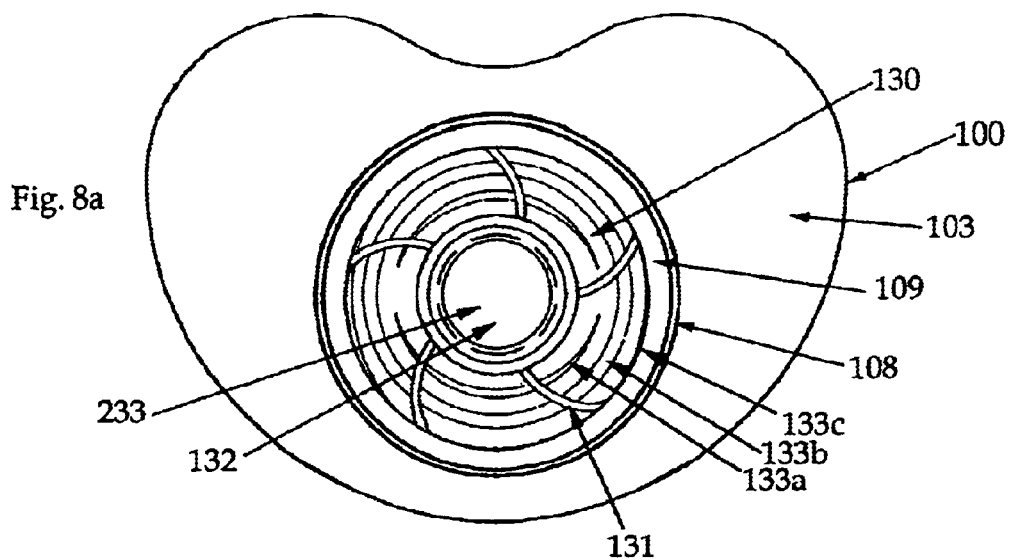
FIG. 8a is a top view of the upper plate of FIG. 3a, with the belleville washer of FIGS. 5a–5c fitted within a retaining wall and a retaining ring of the upper plate.
Figure 8B:
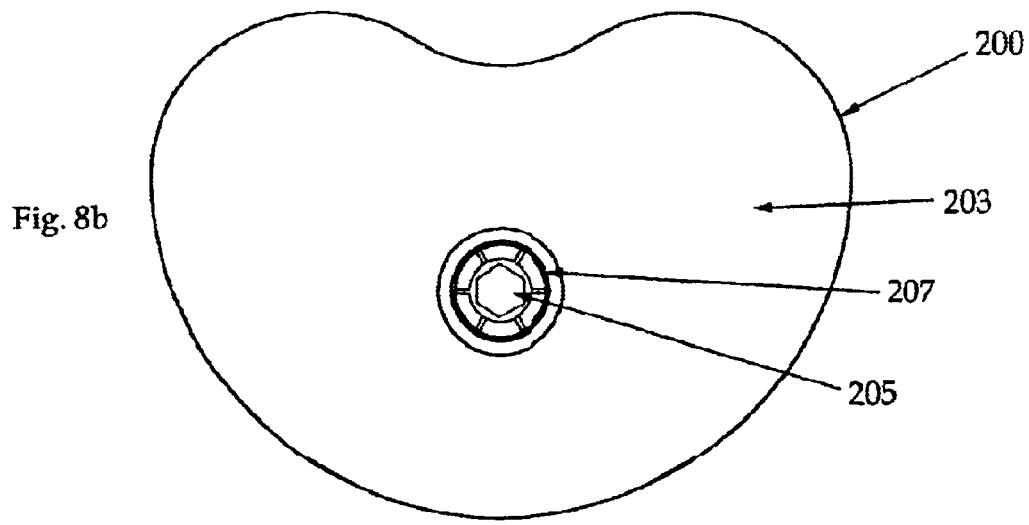
FIG. 8b is a top view of the lower plate of FIG. 3b.

Referring now to FIG. 8a, a top view of the upper plate 100 of FIG. 3a, with the spirally slotted and concentrically grooved belleville washer 130 of FIGS. 5a–5c fitted within a retaining wall 108 and a retaining ring 109 of the upper plate 100, is shown. The diameter of the retaining wall 108 is preferably slightly wider than the diameter of the undeflected belleville washer 130 such that the loading thereof can result in an unrestrained radial deflection of the washer 130. FIG. 8b shows a top view of the lower plate 200 of FIG. 3b.

Figure 9:
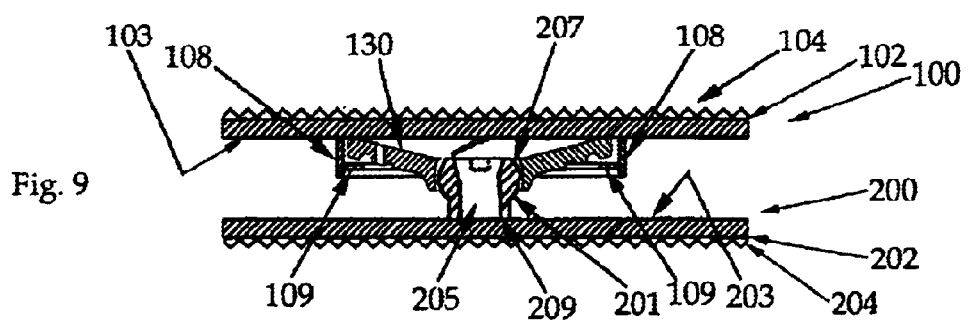
FIG. 9 is a cross-section view of an alternate embodiment of the present invention, which utilizes a belleville washer of the type shown in FIGS. 5a–5c, showing the plates of FIGS. 8a and 8b assembled together.

FIG. 9 shows a fully assembled alternate embodiment of the present invention. The spirally slotted and concentrically grooved belleville washer 130 of FIGS. 5a–5c is placed with its wide end against the top plate 100 within the annular retaining wall 108 as shown in FIG. 6b. The annular retaining ring 109 is provided to hold the belleville washer 130 against the internal face 103 of the upper plate 100 within the retaining wall 108. The post 201 of the lower plate 200 is fitted into the central opening 132 of the belleville washer 130 (the deflectability of the ball-shaped head 207 of the post 201, prior to the insertion of the set screw 205, permits the head 207 to be inserted into the interior volume 233 at the center of the belleville washer 130, and the washer 130 to be rotated into the desired angulation; subsequent introduction of the set screw 205 into the axial bore 209 of the post 201 eliminates the deflectability of the head 207 so that the washer 130 cannot be readily removed therefrom, but can still rotate thereon.). The post head 207 can be locked tightly within the central volume 233 of the belleville washer 130 by the tightening of the set screw 205, to prevent any rotation of the plates 100, 200. Compressive loading of the assembly causes the washer 130 to deflect (with the spiral slots and radially spaced concentric grooves enhancing the deflection) so that the wide end radially expands while being maintained centrally against the upper plate 100 by the retaining wall 108 and the retaining ring 109. When the load is removed, the washer 130 springs back to its original shape.

Inasmuch as the human body has a tendency to produce fibrous tissues in perceived voids, such as may be found within the interior of the present invention, and such fibrous tissues may interfere with the stable and/or predicted functioning of the device, some embodiments of the present invention (although not the preferred embodiment) will be filled with a highly resilient and biologically inert elastomeric material. Suitable materials may include hydrophilic monomers such as are used in contact lenses. Alternative materials include silicone jellies and collagens such as have been used in cosmetic applications.

While there has been described and illustrated specific embodiments of an intervertebral spacer device, it will be apparent to those skilled in the art that variations and modifications are possible without deviating from the broad spirit and principle of the present invention. The invention, therefore, shall not be limited to the specific embodiments discussed herein.

We claim:

1. An intervertebral spacer device comprising:
   first and second plate members, each having first and second plate surfaces thereof, said plates being disposed in a spaced apart relationship such that first ones of said plate surfaces oppose one another, and second ones of said plate surfaces face in opposite directions; and
   at least one restoring force providing element disposed between said first surfaces of said first and second plate members, and disposed such that a compressive load applied to said second surfaces of said first and second plate members is counteracted by said at least one restoring force providing element, said at least one restoring force providing element including at least one belleville washer having at least one radially spaced concentric groove and at least one spiral slot;
   wherein said at least one radially spaced concentric groove in said at least one belleville washer comprises a plurality of radially spaced concentric grooves, and wherein at least one of said plurality of radially spaced concentric grooves in said at least one belleville washer has a length;
   wherein said length forms a closed loop.

2. The device as set forth in claim 1, further comprising disposed on at least one of said first and second plate members a retaining wall in which said at least one restoring force providing element is contained.

3. The device as set forth in claim 1, wherein said at least one belleville washer has a narrow end and a wide end and being oriented such that said wide end is in contact with said first surface of one of said first and second plate members.

4. The device as set forth in claim 1, wherein said at least one of said plurality of radially spaced concentric grooves in said at least one belleville washer has a depth and a width, and at least one of said width and said depth is uniform along said length.

5. The device as set forth in claim 1, wherein the radial spacing of said plurality of radially spaced concentric grooves is uniform.

6. The device as set forth in claim 1, wherein each of said plurality of radially spaced concentric grooves in said at least one belleville washer has a respective length, a respective depth along said respective length, and a respective width along said respective length, and wherein at least one of said depths is different than at least one other of said depths, and wherein at least one of said widths is different than at least one other of said widths.

7. The device as set forth in claim 6, wherein each of said plurality of radially spaced concentric grooves in said at least one belleville washer is at a respective distance from an outer edge of said at least one belleville washer, wherein said depths increase incrementally with decreasing said distances, and said widths increase incrementally with decreasing said distances.

8. The device as set forth in claim 1, wherein said at least one spiral slot in said at least one belleville washer comprises a plurality of spaced apart spiral slots, each of which extends from a locus on a peripheral edge of said at least one belleville washer to a locus which is radially in from said peripheral edge.

9. The device as set forth in claim 1, wherein one of said first and second plate members further comprises a post structure extending outwardly from said first surface of said one of said first and second plate members, and which post structure includes a ball-shaped head.

10. The device as set forth in claim 9, wherein said post structure further includes a threaded bore which extends axially from said ball-shaped head toward said first surface of said one of said first and second plate members, and which bore receives therein a threaded set screw such that prior to an insertion of the set screw therein, said bore permits the ball-shaped head to compress radially inwardly, and such that after the insertion of said set screw said ball-shaped head is not readily radially compressible.

11. The device as set forth in claim 10, wherein said at least one belleville washer further comprises a central opening which includes a curvate volume for receiving and holding therein said ball-shaped head.

12. The device as set forth in claim 11, wherein a tightening of said set screw locks said curvate volume with respect to said ball-shaped head.

* * * * *

UNITED STATES PATENT AND TRADEMARK OFFICE
CERTIFICATE OF CORRECTION

| | | |
|---|---|---|
| PATENT NO. | : 6,863,688 B2 | Page 1 of 1 |
| APPLICATION NO. | : 09/975471 | |
| DATED | : March 8, 2005 | |
| INVENTOR(S) | : James D. Ralph and Stephen Tatar | |

It is certified that error appears in the above-identified patent and that said Letters Patent is hereby corrected as shown below:

\*\*On the cover page, item (63), after "2001", please insert the following --, which is a CIP of 09/968,046 filed on Oct. 1, 2001, now abandoned.--\*\*

Signed and Sealed this

Thirteenth Day of April, 2010

David J. Kappos
*Director of the United States Patent and Trademark Office*